(12) United States Patent
Bernal

(10) Patent No.: US 10,636,325 B2
(45) Date of Patent: *Apr. 28, 2020

(54) SIMULATING EYE SURGERY

(71) Applicant: Bioniko Consulting LLC, Sunny Isles, FL (US)

(72) Inventor: Andres Bernal, Sunny Isles, FL (US)

(73) Assignee: Bioniko Consulting LLC, Sunny Isles, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/456,120

(22) Filed: Jun. 28, 2019

(65) Prior Publication Data
US 2019/0318661 A1 Oct. 17, 2019

Related U.S. Application Data

(63) Continuation of application No. 15/675,841, filed on Aug. 14, 2017, now Pat. No. 10,360,815.

(51) Int. Cl.
*G09B 23/28* (2006.01)
*G09B 23/30* (2006.01)
*A61F 9/007* (2006.01)
*G16H 50/50* (2018.01)
*G16H 40/40* (2018.01)
*A61F 9/008* (2006.01)
*G09B 23/22* (2006.01)

(52) U.S. Cl.
CPC .......... *G09B 23/30* (2013.01); *A61F 9/00736* (2013.01); *G16H 40/40* (2018.01); *G16H 50/50* (2018.01); *A61F 2009/00887* (2013.01); *G09B 23/22* (2013.01)

(58) Field of Classification Search
USPC .......... 434/262, 267, 270, 271, 272
See application file for complete search history.

(56) References Cited

U.S. PATENT DOCUMENTS

| | | | |
|---|---|---|---|
| 5,221,208 | A | 6/1993 | Alexander |
| 5,893,719 | A | 4/1999 | Radow |
| 6,485,142 | B1 | 11/2002 | Sheehy et al. |
| 8,845,334 | B1 | 9/2014 | Stoll |

(Continued)

OTHER PUBLICATIONS

Web-site https://fci-ophthalmics.com/products/cataract-1274/kitaro-kits—Kitaro Kits; FCI Ophthalmics—Copyright 2018—retrieved Oct. 30, 2018.

(Continued)

*Primary Examiner* — Kurt Fernstrom
(74) *Attorney, Agent, or Firm* — Fleit Intellectual Property Law; Gary S. Winer; Paul D. Bianco

(57) ABSTRACT

A model for simulating surgery upon the eye has a posterior and an anterior segment. The posterior segment includes structures corresponding to those of the eye, including a hollow globe and an image of the fundus positioned upon an interior, posterior portion of the globe. A mating portion is peripherally formed about an open end of the globe. The anterior segment also includes structures corresponding to those of the eye, including a translucent lens, and another mating portion peripherally formed about a posterior portion of the anterior segment. The mating portions of the posterior and anterior segments releasably connect the posterior and anterior segments. A vitreous substitute material can be added into the posterior segment and is sealed within when the anterior segment is attached.

22 Claims, 5 Drawing Sheets

(56) References Cited

U.S. PATENT DOCUMENTS

| | | |
|---|---|---|
| 9,437,119 B1 | 9/2016 | Bernal |
| 2009/0111081 A1 | 4/2009 | Nylen |
| 2009/0291423 A1 | 11/2009 | Hara |
| 2016/0098944 A1 | 4/2016 | Lin |
| 2016/0372011 A1 | 12/2016 | Bernal |
| 2019/0051216 A1 | 2/2019 | Bernal |

OTHER PUBLICATIONS

Web-site http://www.phillipsstudio.co.uk/products.htm—Ophthalmic Simulated Surgery; Phillips Studio Eye—Copyright 1995-2017—retrieved Oct. 30, 2018.

Web-site http;//retina2020.com/detached-retina-sugery-inland-empire/—"Detached Retina Surgery Inland Empire", Retina Institute, retrieved Jul. 18, 2017.

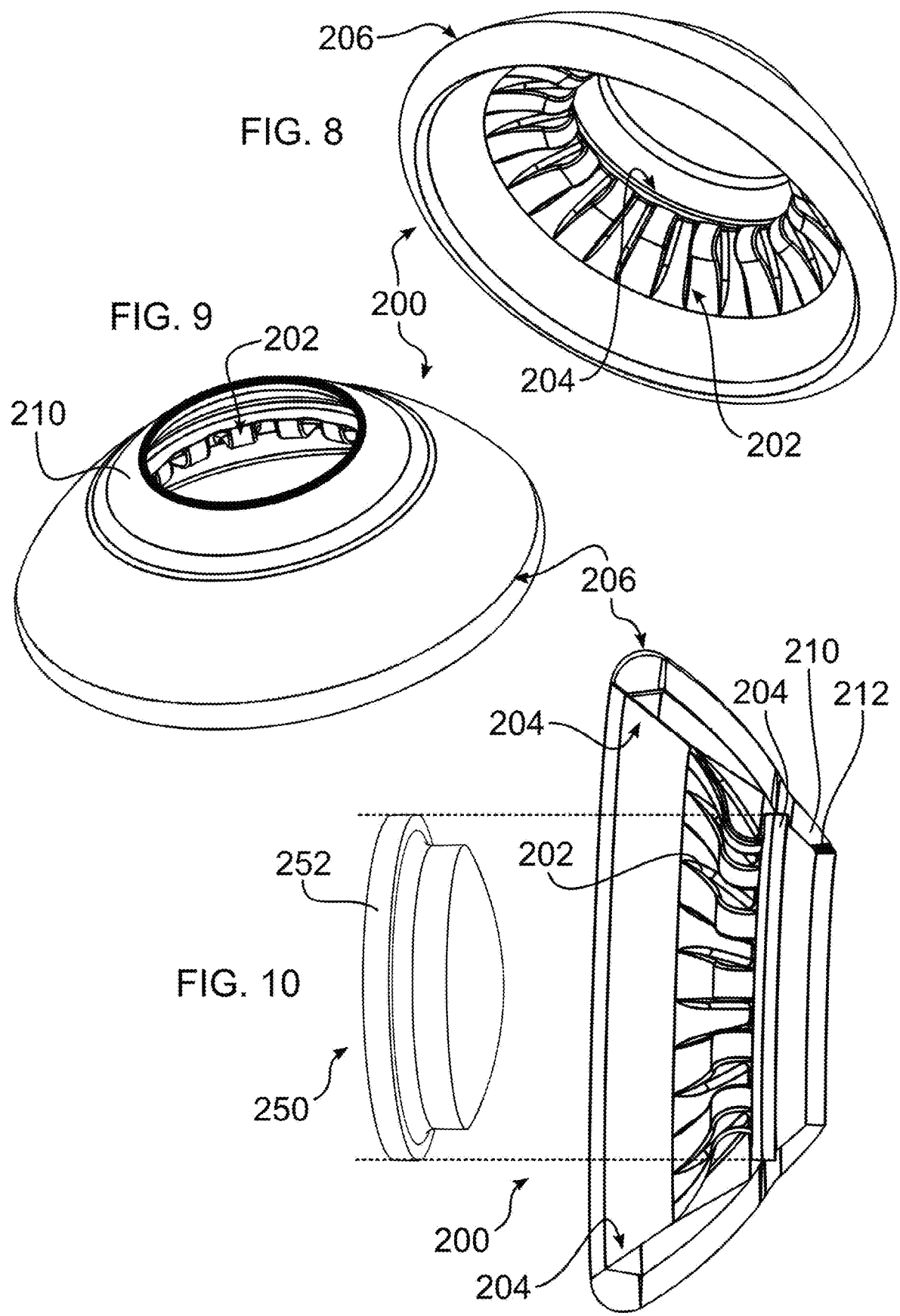

SIMULATING EYE SURGERY

FIELD OF THE DISCLOSURE

The disclosure relates to a system and method for simulating the eye, and in particular, to a physical model which can be used to simulate surgical procedures.

BACKGROUND OF THE DISCLOSURE

Many surgical techniques require dexterous movement and control by the surgeon. This dexterity cannot be developed by reading textbooks or watching instructional videos. Animal models or cadavers have been the default method for hands-on surgical training. In the field of ophthalmic surgery, there are simple examples of a cataract surgery model.

Advances in 3D printing technology allow for the creation of structures with discrete regions having customized mechanical properties. It is possible to print a single object that contains hard components or regions, soft components or regions, and components and regions with properties in-between. This is achieved by the simultaneous deposition of two is complementary materials, one soft and one hard, in controlled proportions, in specific 3D coordinates.

SUMMARY OF THE DISCLOSURE

In an embodiment of the disclosure, a device for simulating surgery upon the eye, comprises a posterior segment including: structures corresponding to those of the eye, including a hollow globe and an image of the fundus positioned upon an interior, posterior portion of the globe; and a first mating portion peripherally formed about an open end of the globe; and an anterior segment including: structures corresponding to those of the eye, including a translucent lens; and a second mating portion peripherally formed about a posterior portion of the anterior segment, the second mating portion mateable with the first mating portion to releasably connect the posterior and anterior segments.

In a variation thereof, the first and second mating portions are dovetail portions; the device further includes a plurality of rectus muscles each attached to the globe at attachment points; the device has an appearance corresponding to the anatomy of a particular species of living organism, the translucent lens having optical properties corresponding to that of the living organism; the first and second mating portions forming a liquid tight seal operative to retain a fluid within the posterior segment and the anterior segment when the first and second portions are mated; the globe is at least partially optically transparent; and/or the lens is releasably retained within the anterior segment.

In further variations thereof, the device further includes a removable coating that is applyable to an interior of the posterior segment; the coating is a liquid which is applyable to the image of the fundus to form a film that will adhere to the fundus when dried, and after drying is peelable from the fundus; the coating includes a substrate and a solubilizing agent; the solubilizing agent is water; air is blown onto the coating after it has been applied to the fundus; and/or the device has an appearance corresponding to the anatomy of a particular species of living organism, the anterior segment including a portion corresponding to the pars plana, the pars plana having a hardness corresponding to that of the living organism, whereby the pars plana is pierceable with a surgical instrument.

In another embodiment of the disclosure, a method of enabling simulation of therapeutic procedures performed upon the eye comprises providing a posterior segment including: structures corresponding to those of the eye, including a hollow globe and an image of the fundus positioned upon an interior, posterior portion of the globe; and a first mating portion peripherally formed about an open end of the globe; providing an anterior segment including: structures corresponding to those of the eye, including a translucent lens; a second mating portion peripherally formed about a posterior portion of the anterior segment, the second mating portion mateable with the first mating portion to releasably connect the posterior and anterior segments; and providing a coating which is applyable to the fundus to form a film that will adhere to the fundus when dried, and after drying is peelable from the fundus in one or more pieces.

In a variation thereof, the coating provided includes a substrate and a volatile solubilizing agent; the method further includes providing instructions for applying the coating to the posterior segment; the substrate is selected from a cellulosic and a polymeric material; the method further includes providing a vitreous substitute material to be placed inside the posterior segment; the method further includes providing instructions for inserting a vitreous substitute material into the posterior segment.

In a further embodiment of the disclosure, a method of simulating a surgical procedure upon the eye comprises separating an anterior segment of a simulated eye from a posterior segment of a simulated eye, the posterior segment including: structures corresponding to those of the eye, including a hollow globe and an image of the fundus positioned upon an interior, posterior portion of the globe; and a first mating portion peripherally formed about an open end of the globe and having the form of one of an annular groove and annular flange; the anterior segment including: structures corresponding to those of the eye, including a translucent lens; a second mating portion peripherally formed about a posterior portion of the anterior segment, the second mating portion mateable with the first mating portion to releasably connect the posterior and anterior segments; inserting a vitreous substitute material into the posterior segment, the substitute material resembling the viscosity and appearance of vitreous humor of a natural eye; and simulating a surgical procedure including removal of vitreous substitute from the eye with the posterior and anterior segments assembled together.

In a variation thereof, the method further includes, prior to inserting a vitreous substitute, applying a coating to a portion of the image of the fundus; and simulating a surgical procedure including manipulating the coating with the posterior and anterior segments assembled together.

In yet another variation thereof, the method further includes providing a viscoelastic substance to be deposited between the first and second mating portions, the substance operative to create a temporary liquid-tight seal.

BRIEF DESCRIPTION OF THE DRAWINGS

A more complete understanding of the present disclosure, and the attendant advantages and features thereof, will be more readily understood by reference to the following detailed description when considered in conjunction with the accompanying drawings wherein:

FIG. 8 is an anterior perspective view of the anterior segment of the model of FIG. 1;

FIG. 9 is a front perspective view of the anterior segment of the model of FIG. 1;

FIG. 10 is a cross-section through a center of the anterior segment of the model of FIG. 1, with the lens removed;

DETAILED DESCRIPTION OF THE DISCLOSURE

Figure 1:
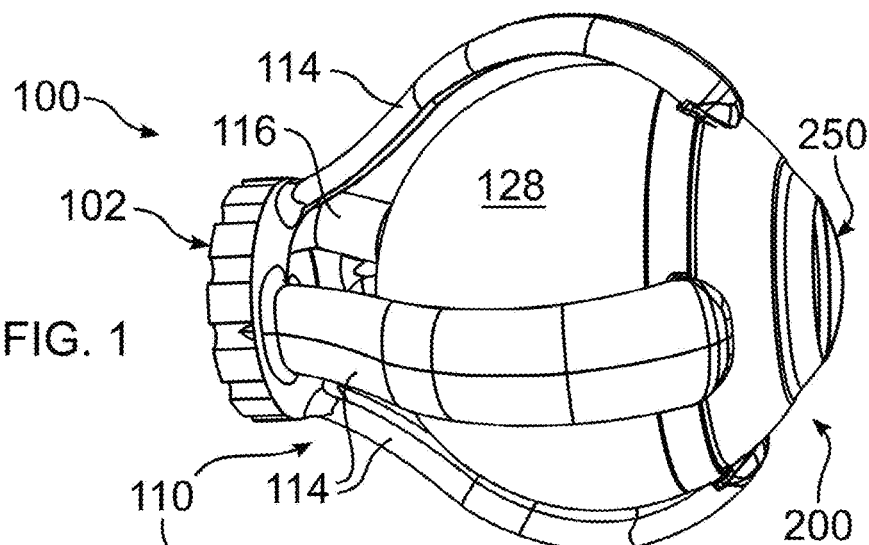
FIG. 1 is a side perspective view of an eye model of the disclosure.

As required, detailed embodiments are disclosed herein; however, it is to be understood that the disclosed embodiments are merely examples and that the systems and methods described below can be embodied in various forms. Therefore, specific structural and functional details disclosed herein are not to be interpreted as limiting, but merely as a basis for the claims and as a representative basis for teaching one skilled in the art to variously employ the present subject matter in virtually any appropriately detailed structure and function. Further, the terms and phrases used herein are not intended to be limiting, but rather, to provide an understandable description of the concepts.

The terms "a" or "an", as used herein, are defined as one or more than one. The term plurality, as used herein, is defined as two or more than two. The term another, as used herein, is defined as at least a second or more. The terms "including" and "having," as used herein, are defined as comprising (i.e., open language). The term "coupled," as used herein, is defined as "connected," although not necessarily directly, and not necessarily mechanically.

The disclosure provides a device 100 which duplicates certain features of a human eye, or the eye of other organisms which are similar to the human eye. The device, having certain features of an anatomical model, mimics or is similar in appearance and mechanical properties to the eye and associated structures, and can be used to understand eye pathology, and for surgical training, demonstration, teaching aids, surgical instrument calibration, validation, and research and development. Device 100 may also be used together with other models for craneo-facial surgery, as a crash test dummy component, or as a ballistic impact model, for example.

Device 100 replicates the mechanical properties of tissues of the eye. More particularly, except for fluid connective tissue, such as blood and lymph, a tissue matrix of the body can be mechanically simplified as being made of two materials, collagen and elastin. Collagen is the material that confers strength, and elastin is the material that confers elasticity. The proportion of elastin and collagen type fibers in the matrix of a tissue can be related to its mechanical properties. Tissue structures predominantly composed of collagen tend to be tough and rigid. Tissue where elastin predominates is more elastic.

As discussed in greater detail in U.S. Patent Pub. 2016/0372011 and U.S. Pat. No. 9,437,119, the contents of which are incorporated herein by reference, the inventor has found that the an eye model can be produced by 3D multi-material printing, whereby different tissues of the eye can be represented by particular materials during printing. In this manner, the texture and appearance of the particular structures can be reproduced within the model. As one example, as discussed elsewhere herein, a trocar is inserted into the anterior portion of the eye. The anterior segment of device 100 is fabricated using a material which responds in a is similar manner to eye tissue, when pierced by a trocar, for example yielding in a similar manner, and retaining an access port in a similar manner.

For example, the eye can conveniently be considered as being composed of collagen type tissue, and elastin type tissue, where a different material can be used to produce each type of tissue. However, regardless of how various tissues in the eye are classified with respect to collagen or elastin, materials printed are ultimately selected to have a hardness and resiliency which mimics structures of the natural organ. More particularly, materials are selected whereby the resultant tissue simulation behaves in a manner similar to a live or donor eye, with respect to resistance to pressure, piercing and cutting, burning/ablation, manipulation, and other applications of force, as well as physical appearance. The 3D printed materials, or materials used in other types of manufacturing processes, are therefore selected to best represent the properties of the tissue to be reproduced in device 100.

While 3D printing is one method to device 100, it should be understood that other manufacturing methods can be used, including casting, molding, machining, and other known or hereinafter developed methods.

Figure 2:
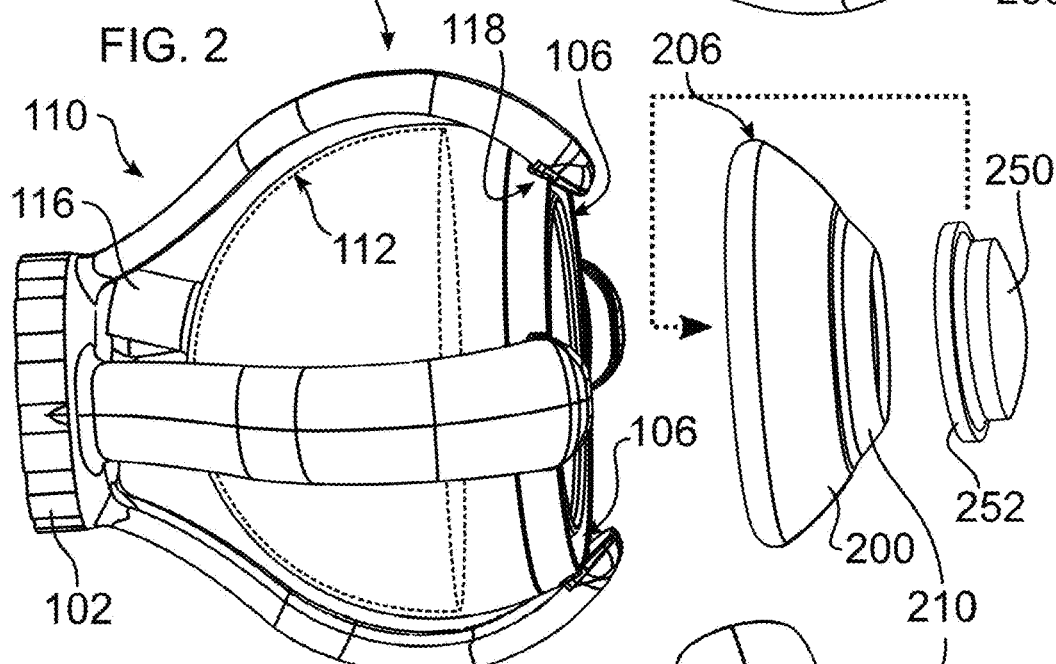
FIG. 2 is an exploded view of the model of FIG. 1.
Figure 3:
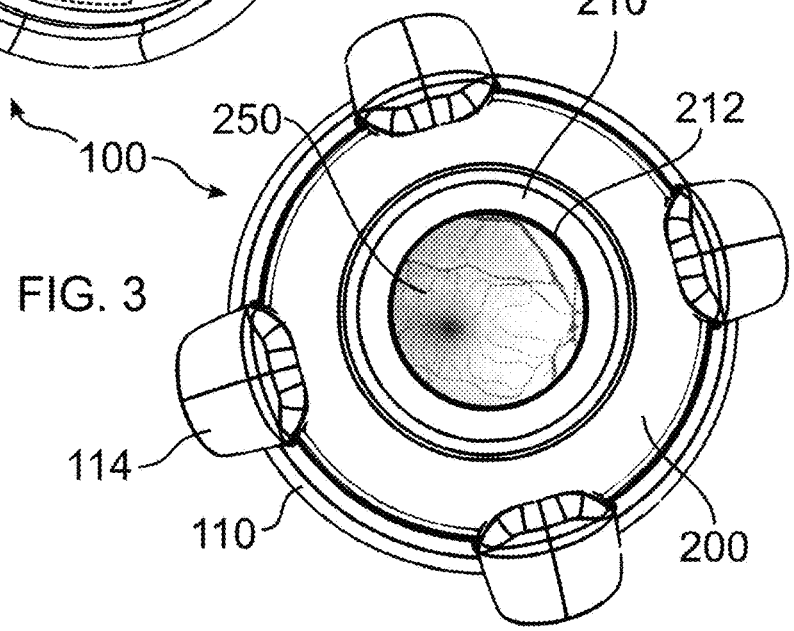
FIG. 3 is a front view of the model of FIG. 1.
Figure 4:
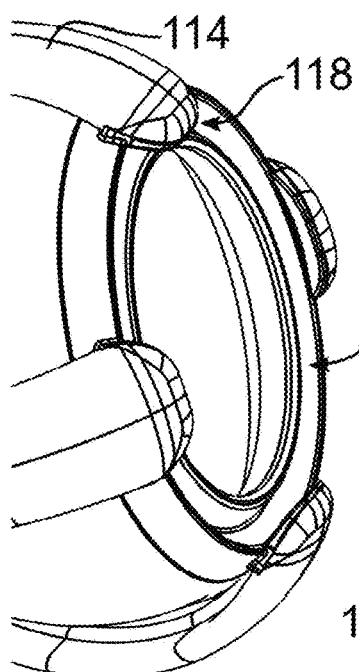
FIG. 4 is perspective view of the model of FIG. 1, with the anterior segment removed.

With reference to FIGS. 1-3, device 100 includes a support base 102, a posterior segment 110 including an area corresponding to the ora serrata and structures posterior to it, an anterior segment 200 including an area corresponding to the pars plana and the structures anterior to it. A corneal rim 210 and iris 212 are visible upon an exterior surface of anterior segment 200. Posterior segment 110, forming the globe 128, is connected to base 102 by one or more rectus muscles 114. An optic nerve 116 extends from the posterior segment to base 102. It should be understood that the boundary between the posterior and anterior segments 110, 200 can be different, for example, the ora serrata or other structure can be included in anterior segment 200. However, as described further elsewhere herein, the interior of the globe portion of the eye can be filled with a vitreous component which is conveniently retained in the posterior segment.

Figure 5:
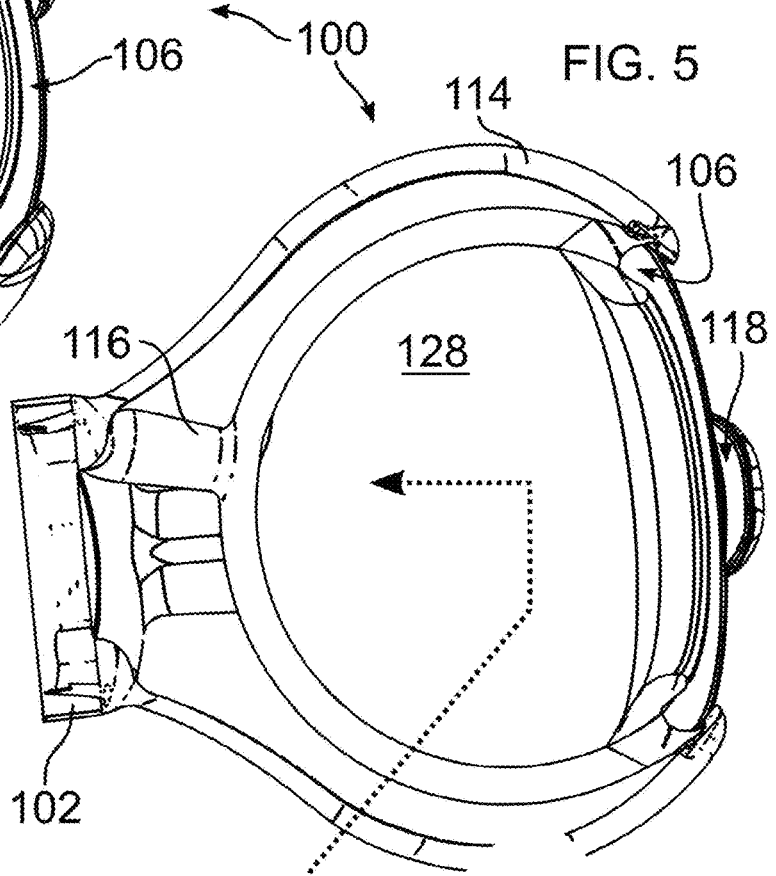
FIG. 5 is a longitudinal cross-section through the model of FIG. 1.
Figure 6:
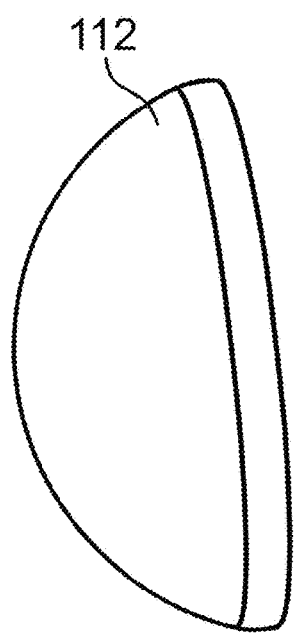
FIG. 6 is a removable fundus positionable within the model of FIG. 1.
Figure 7:
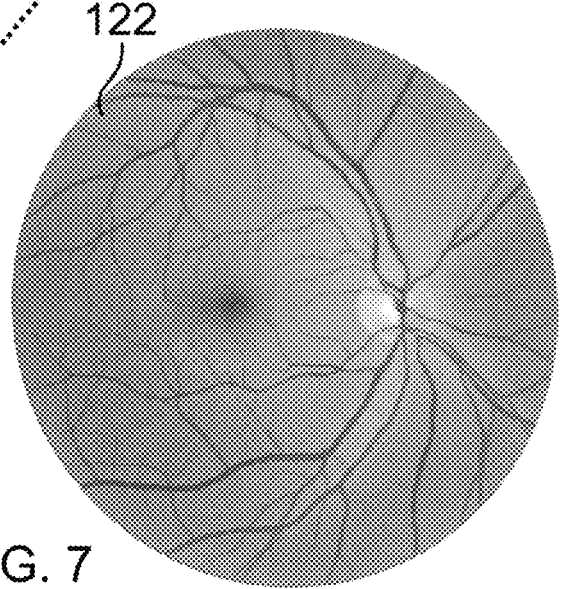
FIG. 7 is a flexible substrate printed with an image of the fundus, positionable within the model of FIG. 1.
Figure 11:
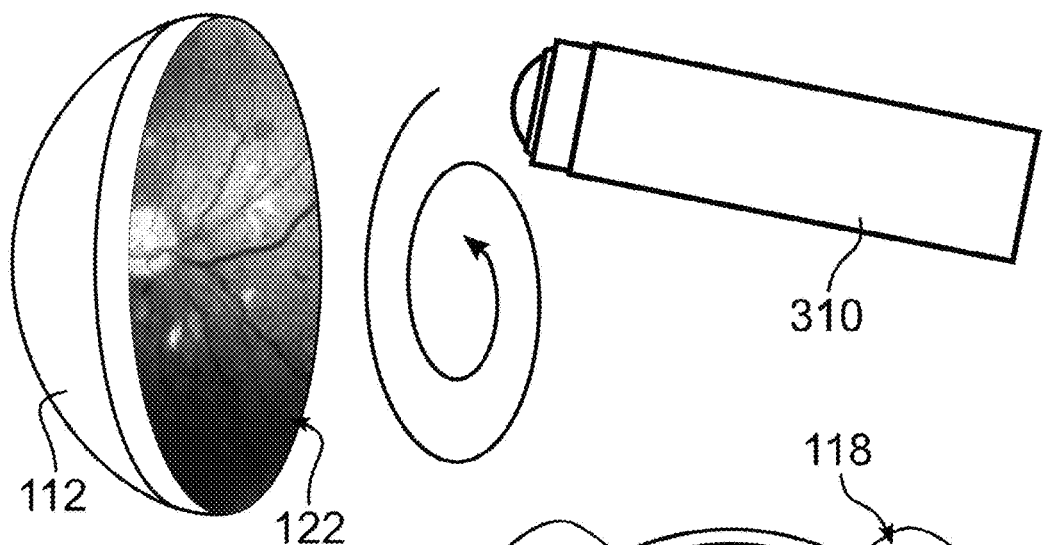
FIG. 11 depicts a manner of coating a fundus area of the model of FIG. 1.

With additional reference to FIGS. 5-7, the posterior segment includes the retinal fundus and associated structures, including the retina, optic disc, vasculature/arcade, and macula, which may be formed in part as a separate, removable fundus part 112 as shown in dashed lines in FIG. 2, and in FIGS. 7, and 11, or may be removable but integrally formed by 3D printing during fabrication of anterior portion 110, or alternatively may be formed integrally with a posterior portion of the eye. Structures visible at the back of the eye, such as the macula, retinal vasculature, and optic disc, can be printed during 3D printer fabrication onto removable fundus part 112, or can be printed directly onto a fundus location of the eye where part 112 is integral, or may be separately printed onto a flexible substrate 122 (FIG. 7), which is secured in place after 3D printing.

As shown in FIG. 2, and with reference to FIGS. 8-10, an optical element or lens 250 is inserted within anterior segment 200 to lie between structures resembling suspensory ligaments and ciliary bodies 202 (visible in FIGS. 8-9). Lens 250 can be provided with a focal length which approximates that of the particular eye the model is replicating, for example that of a human eye. Lens 250 includes a posterior ridge 252 which is provided to seat the lens within at location with respect to the retina which approximates that of the eye. A corresponding mating annular groove or ridge 204 is provided within anterior segment 200. Due to a flexibility of anterior segment 200, corresponding to the natural resiliency of the body, mating ridge 204 can be sized to form an interference fit with posterior ridge 252, and therefore resiliently grips posterior ridge 252 when the latter has been inserted into mating engagement with mating groove 204. In this manner, lens 250 is inserted into mating engagement by being inserted through the interior portion of anterior segment 200, as shown by the dashed arrow of FIG. 2. Lens 250 is advantageously handled using gloves, to avoid introducing fingerprints or other markings onto lens 250.

It should be understood that, alternatively, anterior segment 200 can be provided with a ridge and lens 250 can be provided with a groove, or that any other kind of dovetail or interlocking engagement can be formed between the anterior segment 200 and lens 250, including for example threaded engagement. Alternatively or additionally, the ciliary bodies 202 or processes can be formed to partially interfere with passage of lens 250 into a final position, and to retain lens 250 in position. As such, lens 250 can be pushed past such interference by pressing about the periphery of the lens.

In the embodiment illustrated, lens 250 is dimensioned to form both the lens and the cornea, although these can be provided as separate structures, if desired. If provided as separate structures, an iris can be provided to be positioned between the lens and cornea, or can alternatively be provided behind the combined lens and cornea to render a similar effect.

Anterior segment 200 is provided with an annular peripheral flange or ridge 206 which matingly engages a corresponding annular groove 106 formed within an anterior portion of posterior segment 200. Posterior segment 110 is printed to have a resilient property similar to the eye; as such, groove 106 can be elastically stretched to admit passage of ridge 206. It should be understood that, alternatively, anterior segment 200 can be provided with a groove and posterior segment 110 with a ridge, or that any other kind of dovetail or interlocking engagement can be formed between the anterior and posterior segments 200, 110, including for example a threaded engagement.

One or more of the muscle attachments 118 additionally overlap anterior segment 200. More particularly, in one embodiment, muscle attachments 118 are fixed to posterior segment 110, and retain anterior segment 200 anteriorly by projecting anteriorly and inward to extend past and over the anterior segment. In this manner, a retaining or a clamping force is applied between the anterior and posterior segments 110, 200, so that a seal can be maintained between anterior and posterior segments 110, 200. This enables not only removal of anterior segment 200, but replacement of anterior segment 200 as needed. For example, anterior segment can be pierced by trocars, as described elsewhere herein, and may eventually need to be replaced for this or other reasons, which is facilitated by the releasable connection formed by the seal between annular ridge 206 and annular groove 106, and the cooperating engagement of one or more muscle attachments 118, as described above.

As shown in FIG. 3, once lens 250 has been assembled into anterior segment 200, and anterior segment 250 has been assembled into posterior segment 110, the fundus and associated structures can be viewed by looking through lens 250.

As lens 250, anterior segment 200, and posterior segment 110 can be independently replaced, device 100 forms a platform that is reusable, where parts subject to wear or damage can be replaced as needed, and where lesser affected parts can continue to be reused.

With reference to FIG. 11, device 100 can be used to train a surgeon to remove a thin film from a surface of the interior of the eye. One such example is Internal Limiting Membrane (ILM) peeling. In accordance with the disclosure, a coating 304 (FIG. 13) is applied to the retinal surface. In the embodiment shown, the coating is applied using a roll-on applicator 300, although other methods can be used, including brush or spray applicator. In order to provide for quick drying, a volatile solvent can be mixed with the coating to maintain the coating in a liquid state within the dispenser, and while dispensing. As the solvent evaporates, the coating dries and adheres to the substrate, which in the example shown is retinal part 112. Once the coating has applied, the solvent will evaporate over time, or a stream of air can be directed against the coating to hasten drying. Once the coating has dried, it is ready to be peeled from the eye in a mock surgical procedure.

Any coating material can be used which has properties resembling naturally occuring membranes which are desired to be removed. Such properties include an adhesion to the retinal or other surface of the eye which is sufficiently weak to allow peeling without damage to the underlying structure. Additionally, the dried coating must be sufficiently cohesive as to be peelable in strips, as occurs within the body. Such a coating material can be produced combining any substrate material, such as a cellulosic or polymeric material, with a solvent which renders or maintains the substrate material in liquid form, and which exhibits the desired properties when present in the eye. One or more dyes or colorants can be added to the base coating, in order to simulate either a typical color of naturally occurring membranes, or any of the various dye colorings used in such surgical peeling procedures.

For clarity, part 112 is illustrated as removed from posterior segment 110. As a practical matter, there is no need to remove part 112 to apply the coating, as roll-on applicator 300 can be readily manipulated against the retinal surface after having removed only the anterior segment 200. A spiral arrow is illustrated in FIG. 11 to demonstrate that it is typically desired to apply the coating evenly over the surface, to mimic the natural growth of undesired membranes. Any pattern of application can be used, however, and overlapping can be carried out to increase a thickness of all or a portion of the applied coating. An overlap or thicker region relative to surroundings can be deliberately formed, for example, in order to facilitate an initial grasp of the membrane for peeling, during training. Irregularities can alternatively be formed by applying bursts of air, for example using compressed air from a spray can. To apply a thicker coating, a cotton swab may be used instead of a roll-on applicator.

The coating may be removed by using a cotton swab moistened with water or a solvent, and the fundus can be dried, for example in preparation for applying a new coating, by the application of a jet of air.

The foregoing coating can additionally be removed by the application of laser light energy, for example, and a coating can be selected which responds to the application of laser light in a manner similar to materials removed by laser in actual therapeutic practice.

Figure 12:
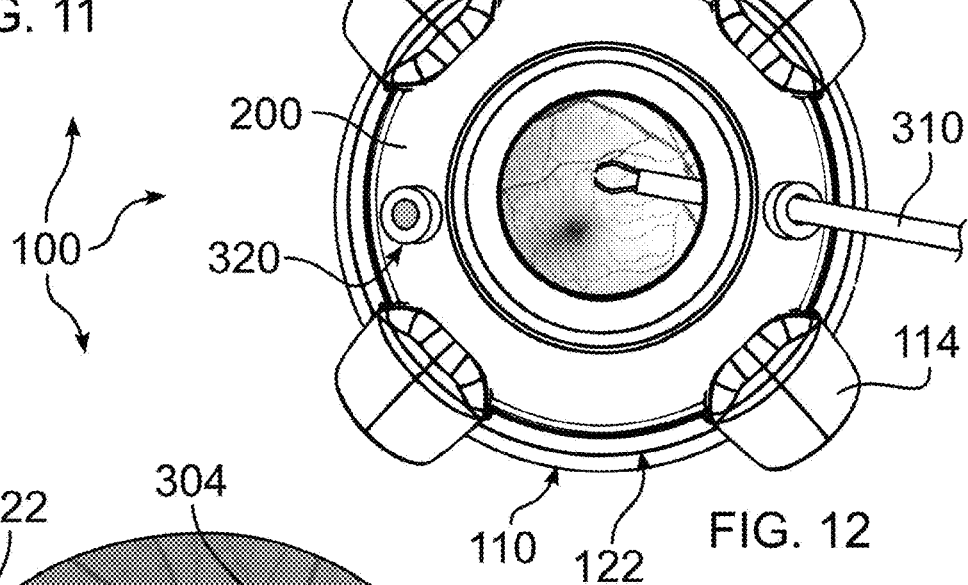
FIG. 12 depicts a manner of manipulating the model of FIG. 1 with a surgical instrument.
Figure 13:
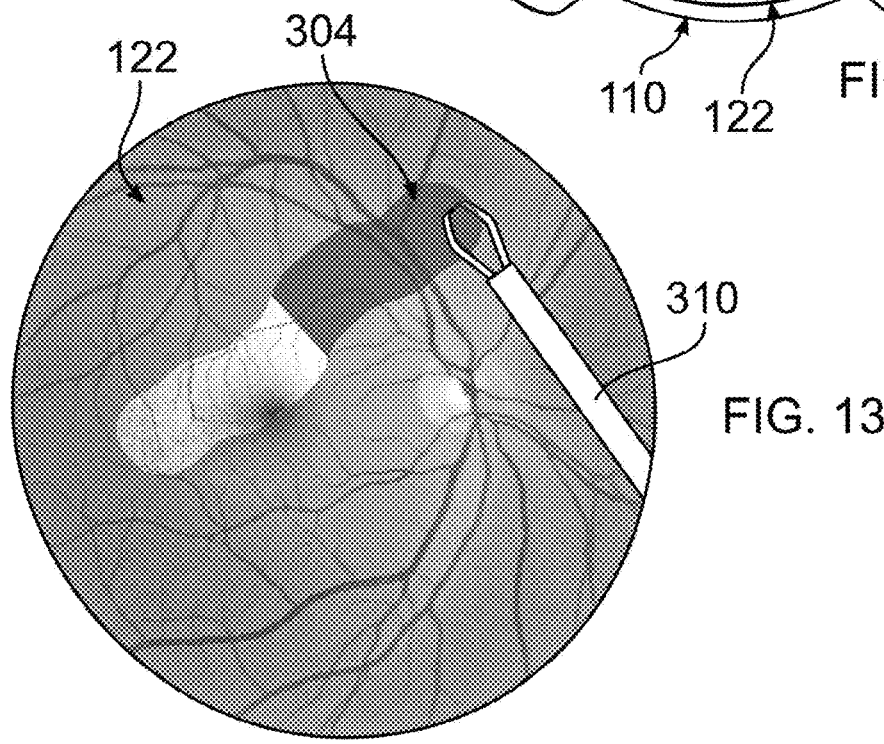
FIG. 13 depicts peeling of the coating of FIG. 11 using the instrument of FIG. 12.
Figure 16:
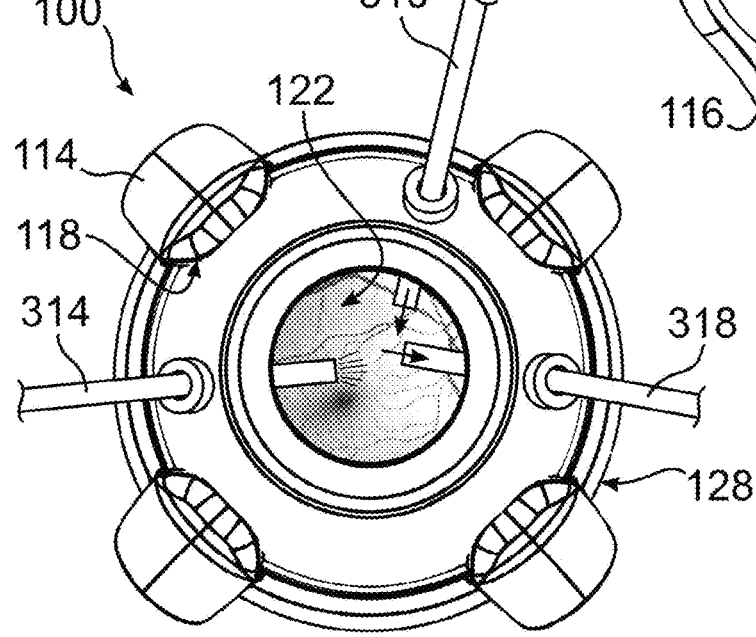
FIG. 16 depicts removing a vitreous substance from within the model of FIG. 1.

As shown in FIGS. 12-13, a trocar or other piercing instrument can be used to insert a portal in a surface of the eye, through which forceps 310 or other instrument may be passed, and through which separated/peeled membrane (coating), or other objects, can be removed from the eye. Additional ports may be provided for other instruments, as described with respect to vitreous replacement, and as shown in FIG. 16.

Figure 14A:
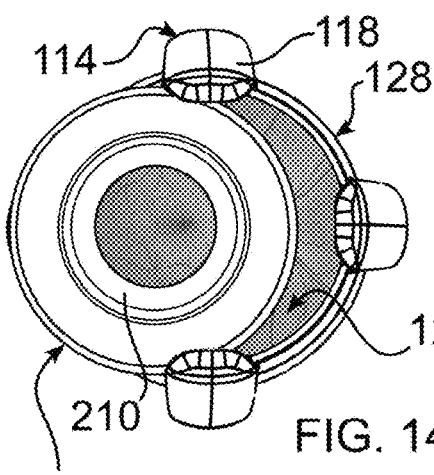
FIG. 14A depicts assembly of the anterior segment onto the model of FIG. 1, initially laterally moving the anterior segment under two muscle attachments.
Figure 14B:
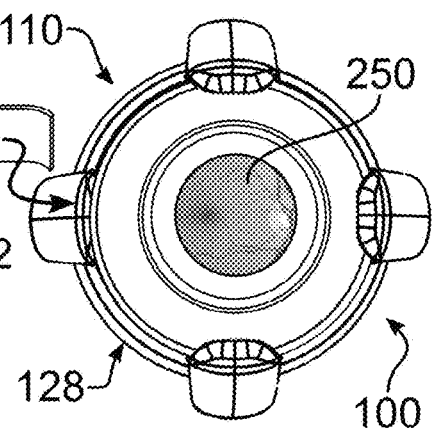
FIG. 14B depicts a further assembly step, subsequent to the step of FIG. 14A, in which the anterior segment is positioned under three muscle attachments.

In FIGS. 14A-14B, anterior segment 250 is assembled onto posterior segment 110. As shown, anterior segment 250 is at first inserted under two opposing muscle attachments 118 (FIG. 14A), and then moved laterally until it is positioned under three muscle attachments 118 (FIG. 14B). The final muscle attachment 118 can be pried from under anterior segment 250 with a slim object, such as a plastic spudger, or a curved-ended tool 312 as shown, which is turned over from the view shown, inserted between the remaining muscle attachment 118 and anterior segment 250, and rotated end-over-end to move the muscle attachment over anterior segment 250. Once this has been accomplished, peripheral ridge 206 may be pushed downward to be inserted into groove 106 of posterior segment 110.

To facilitate insertion, ridge 206 and/or groove 106 can be lubricated with a peripheral bead of viscoelastic sealant, which may or may not additionally have a lubricating property, water, or other sealant which is not harmful to the materials forming device 100. Dispersive viscoelastics are made by variety of manufacturers, particularly in the eye care field. The use of viscoelastic seal is advantageously helpful in ensuring a liquid tight seal between posterior segment 110 and anterior segment 250, avoiding a requirement for a threaded seal, or the use of o-rings or other gasket. Other sealant materials include silicones, caulking, petroleum jelly, sealing grease, and a weak adhesive that is releasable without damaging the sealed components.

Figure 14C:
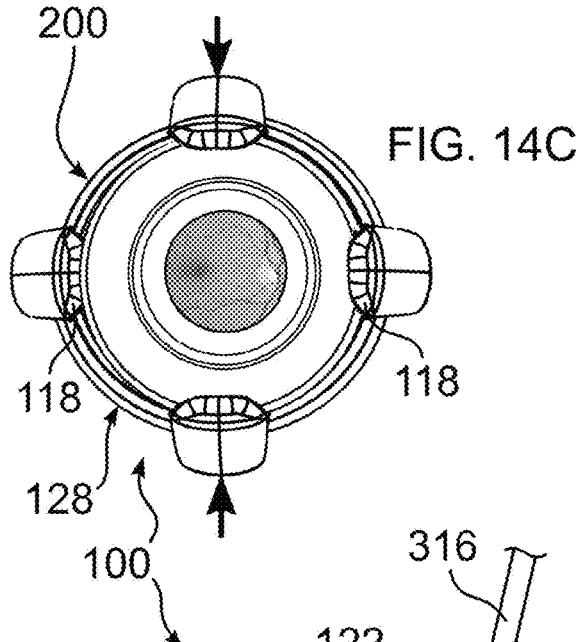
FIG. 14C depicts compressing the model in order to expose a portion of the fourth muscle attachments, in order to facilitate moving the fourth muscle attachment above the anterior segment.

As shown in FIG. 14C, the fourth muscle insertion can be more easily moved above anterior segment 200 by gently squeezing globe 128 to elongate the globe along an axis passing through the fourth muscle insertion 118. This technique can be used to carry out assembly without the use of a tool.

To disassemble anterior segment 250 from posterior segment 110, lens 250 is first pushed into the interior of the globe. Next, the anterior segment is grasped by inserting one finger through the aperture opened by removal of the lens, and pinching the anterior segment between two fingers, whereupon it may be pulled away from and free of posterior segment 110. Alternatively, a tool can be provided which includes rounded or soft ends, which can be inserted through the iris and levered against the inside of anterior segment 250 to cause separation of anterior segment 250 from posterior segment 110.

Figure 15:
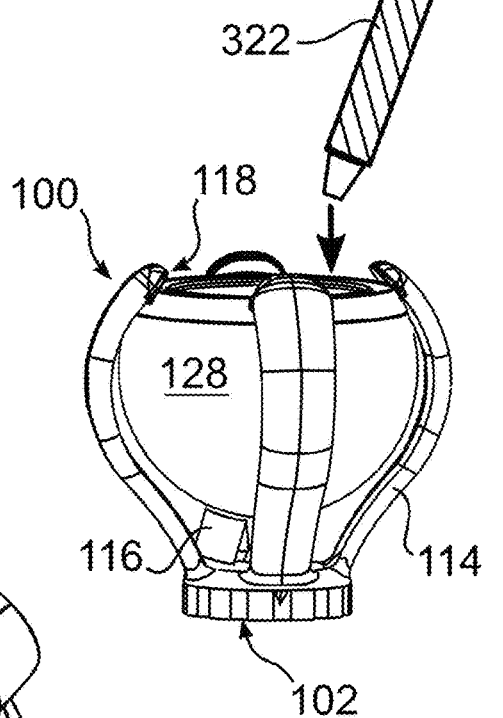
FIG. 15 depicts filling the posterior segment of the model of FIG. 1.

Referring now to FIGS. 15-16, device 100 may be filled with a vitreous substance which is similar in appearance and opacity, and viscosity, to naturally occurring vitreous humor for the type of eye being simulated. A convenient material is egg whites from a chicken egg, or materials having similar appearance and viscosity to egg whites, including any other material which is advantageously not harmful to the materials from which device 100 is fabricated. As shown, a syringe 322 may be used to draw up egg whites from a containment vessel, and to load the egg whites into the eye. As shown, anterior segment 250 is removed to expose the eye interior. In an embodiment sized to represent a human eye, about 3 cc of egg whites are used, although different amounts can be used dependent upon the size of the interior of device 100, to correspond to filling of a natural eye. Care is taken to introduce the vitreous substitute slowly, to avoid introducing bubbles. If bubbles do form, they may be aspirated to remove them before replacing the anterior segment as described herein.

As shown in FIG. 16, a surgical procedure can be carried out using device 100, which procedure is more realistic once a vitreous substance has been added to the eye. In particular, a vitrectomy can be performed, to remove all or a portion of the vitreous substitute. As shown, three ports 320 have been formed, including a port 320 each for admitting an instrument for illumination 314, an injection instrument 316 to introduce air or liquid to maintain internal eye pressure, and a cutter or aspirator instrument 318 to remove the vitreous humor/substitute, or other material or object from the eye. Other procedures which may be simulated include, but are not limited to, addressing retinal detachment, macular pucker, diabetic retinopathy, macular holes, vitreous hemorrhage, and vitreous floaters. As needed, objects can be deliberately introduced into the eye, together with the vitreous substitute, to enable training for certain procedures. Such procedures can be facilitated by the application of retro-illumination through globe 128.

In an embodiment of the disclosure, globe 128 is at least partly translucent, enabling light transmission, and retro-illumination. An Iris of any desired size can be produced, for example between 1 and 8 mm, and lens 250 can be provided in various optical powers, with various coatings. Additionally, the fundus can be printed with various pathologies, or a plurality of flexible substrate 122 can be provided, each illustrating a different pathology. In an embodiment, lens 250 has an optical power between 40 and 60 diopters, although a larger or smaller range can be used, dependent upon the optical power of the natural eye which is being simulated, or a power selected to facilitate simulating surgery with device 100.

Accordingly, the disclosure provides a simulation and model, device 100, for anterior and posterior segment training and simulation. Device 100 facilitates training in basic retinal examination technique and instrumentation such as indirect ophthalmoscopy, slit-lamp, contact and non-contact retinal lenses, and retinal cameras. It is also an useful tool for demonstration, practice and assessment of retinal instrument handling and microscope skills such as use of surgical contacts lenses, non-contact systems and inverters. The modular design of device 100 allows insertion of foreign bodies or vitreous substitutes to enhance training scenarios. It also allows simplifications such as optical element removal and trans-illumination to facilitate practice where vitreo-retinal equipment is unavailable.

All references cited herein are expressly incorporated by reference in their entirety. It will be appreciated by persons skilled in the art that the present disclosure is not limited to what has been particularly shown and described herein above. In addition, unless mention was made above to the contrary, it should be noted that all of the accompanying drawings are not to scale. There are many different features to the present disclosure and it is contemplated that these features may be used together or separately. Thus, the disclosure should not be limited to any particular combination of features or to a particular application of the disclosure. Further, it should be understood that variations and modifications within the spirit and scope of the disclosure might occur to those skilled in the art to which the disclosure pertains. Accordingly, all expedient modifications readily attainable by one versed in the art from the disclosure set forth herein that are within the scope and spirit of the present disclosure are to be included as further embodiments of the present disclosure.

What is claimed is:

1. A device for simulating surgery upon the eye, comprising:
    a posterior segment including:
        structures corresponding to those of the eye, including a hollow globe and an image of the fundus positioned upon an interior, posterior portion of the globe; and
        a first mating portion peripherally formed about an open end of the globe; and
    an anterior segment including:
        structures corresponding to those of the eye, including a translucent lens; and
        a second mating portion peripherally formed about a posterior portion of the anterior segment, the second mating portion mateable with the first mating portion to releasably connect the posterior and anterior segments.

2. The device of claim 1, wherein the first and second mating portions are dovetail portions.

3. The device of claim 1, further including a plurality of rectus muscles each attached to the globe at attachment points.

4. The device of claim 1, the device having an appearance corresponding to the anatomy of a particular species of living organism, the translucent lens having optical properties corresponding to that of the living organism.

5. The device of claim 1, the first and second mating portions forming a liquid tight seal operative to retain a fluid within the posterior segment and the anterior segment when the first and second portions are mated.

6. The device of claim 1, wherein the globe is at least partially optically transparent.

7. The device of claim 1, wherein the lens is releasably retained within the anterior segment.

8. The device of claim 1, further including a removable coating that is applyable to an interior of the posterior segment.

9. The device of claim 8, wherein the coating is a liquid which is applyable to the image of the fundus to form a film that will adhere to the fundus when dried, and after drying is peelable from the fundus.

10. The device of claim 9, wherein the coating includes a substrate and a solubilizing agent.

11. The device of claim 9, wherein the solubilizing agent is water.

12. The device of claim 9, wherein air is blown onto the coating after it has been applied to the fundus.

13. The device of claim 1, the device having an appearance corresponding to the anatomy of a particular species of living organism, the anterior segment including a portion corresponding to the pars plana, the pars plana having a hardness corresponding to that of the living organism, whereby the pars plana is pierceable with a surgical instrument.

14. A method of enabling simulation of therapeutic procedures performed upon the eye, comprising:
    providing a posterior segment including:
        structures corresponding to those of the eye, including a hollow globe and an image of the fundus positioned upon an interior, posterior portion of the globe; and
        a first mating portion peripherally formed about an open end of the globe;
    providing an anterior segment including:
        structures corresponding to those of the eye, including a translucent lens; and
        a second mating portion peripherally formed about a posterior portion of the anterior segment, the second mating portion mateable with the first mating portion to releasably connect the posterior and anterior segments; and
    providing a coating which is applyable to the fundus to form a film that will adhere to the fundus when dried, and after drying is peelable from the fundus in one or more pieces.

15. The method of claim 14, wherein the coating provided includes a substrate and a volatile solubilizing agent.

16. The method of claim 14, further including providing instructions for applying the coating to the posterior segment.

17. The method of claim 15, wherein the substrate is selected from a cellulosic and a polymeric material.

18. The method of claim 14, further including providing a vitreous substitute material to be placed inside the posterior segment.

19. The method of claim 14, further including providing instructions for inserting a vitreous substitute material into the posterior segment.

20. A method of simulating a surgical procedure upon the eye, comprising:
    separating an anterior segment of a simulated eye from a posterior segment of a simulated eye, the posterior segment including:
        structures corresponding to those of the eye, including a hollow globe and an image of the fundus positioned upon an interior, posterior portion of the globe; and
        a first mating portion peripherally formed about an open end of the globe and having the form of one of an annular groove and annular flange;
    the anterior segment including:
        structures corresponding to those of the eye, including a translucent lens;
        a second mating portion peripherally formed about a posterior portion of the anterior segment, the second mating portion mateable with the first mating portion to releasably connect the posterior and anterior segments;
    inserting a vitreous substitute material into the posterior segment, the substitute material resembling the viscosity and appearance of vitreous humor of a natural eye; and simulating a surgical procedure including removal of vitreous substitute from the eye with the posterior and anterior segments assembled together.

21. The method of claim 20, further including, prior to inserting a vitreous substitute, applying a coating to a portion of the image of the fundus; and simulating a surgical procedure including manipulating the coating with the posterior and anterior segments assembled together.

22. The method of claim 20, further including providing a viscoelastic substance to be deposited between the first and second mating portions, the substance operative to create a temporary liquid-tight seal.

* * * * *